United States Patent [19]

Fryer et al.

[11] 3,931,225

[45] Jan. 6, 1976

[54] PROCESS FOR PREPARING O-NITROBENZYLKETONES

[75] Inventors: Rodney Ian Fryer, North Caldwell; Edward Ernest Garcia, West Caldwell, both of N.J.

[73] Assignee: Hoffmann-La Roche Inc., Nutley, N.J.

[22] Filed: Jan. 21, 1974

[21] Appl. No.: 435,050

[52] U.S. Cl.... 260/326 N; 260/293.71; 260/293.72; 260/293.8; 260/326.5 J; 260/326.87; 260/570.5 C; 260/570.8; 260/590

[51] Int. Cl.$^2$................. C07D 209/48; C07C 49/76

[58] Field of Search.......... 260/326 N, 590, 570.5 C

*Primary Examiner*—Lewis Gotts
*Assistant Examiner*—S. P. Williams
*Attorney, Agent, or Firm*—Samuel L. Welt; Bernard S. Leon; William G. Isgro

[57] ABSTRACT o-nitrobenzylketones are prepared by reacting a trans-β-substituted amino-2-nitrostyrene with a lower alkanoyl halide, halo-lower alkanoyl halide, phthalimido-lower alkanoyl halide, benzoyl halide or substituted benzoyl halide, and subsequently hydrolyzing the resulting product to yield the desired o-nitrobenzylketone.

3 Claims, No Drawings

PROCESS FOR PREPARING O-NITROBENZYLKETONES

BRIEF SUMMARY OF THE INVENTION

The invention relates to a process for preparing o-nitrobenzylketones, which comprises the steps of:

a. reacting a trans-$\beta$-substituted amino-2-nitrostyrene of the formula

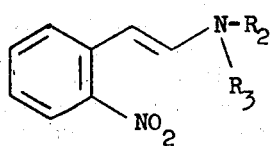   III wherein $R_2$ and $R_3$, independently, are lower alkyl or when taken together, are lower alkylene, with a lower alkanoyl halide, halo-lower alkanoyl halide, phthalimido-lower alkanoyl halide, benzoyl halide or substituted benzoyl halide to yield the corresponding compound of the formula

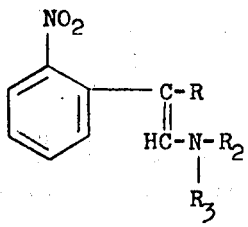   II wherein R is lower alkanoyl, halo-lower alkanoyl, phthalimidolower alkanoyl, benzoyl or substituted benzoyl; and $R_2$ and $R_3$ are as previously described, and subsequently, b. hydrolyzing the product of step (a) whereby the corresponding o-nitrobenzylketone of the formula

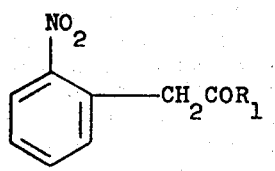   I wherein $R_1$ is lower alkyl, halo-lower alkyl, phenyl, substituted phenyl or phthalimido-lower alkyl,
is obtained.

In another aspect, the invention relates to the novel intermediates of formula II.

The o-nitrobenzylketones are useful as intermediates in the preparation of 2-substituted-indoles. More particularly, the o-nitrobenzylketones are chemically or catalytically reduced to the desired 2-substituted indoles.

DETAILED DESCRIPTION OF THE INVENTION

The invention relates to a process for preparing o-nitrobenzylketones.

As used herein, the term "lower alkyl" denotes a straight or branched chain saturated hydrocarbon of 1 to 7 carbon atoms, for example, methyl, ethyl, propyl, isopropyl, butyl, t-butyl, neopentyl, pentyl, heptyl, and the like. The term "halogen" denotes all the halogens, i.e., bromine, chlorine, fluorine and iodine. The term "lower alkanoyl" denotes a group derived from an aliphatic carboxylic acid of 2 to 7 carbon atoms, for example, acetyl, propionyl, and the like. The term "lower alkylene" denotes a hydrocarbon radical of two to five carbon atoms, such as, ethylene, propylene, butylene and pentylene. The term "substituted benzoyl" denotes a benzoyl moiety having 1 to 3 of its hydrogen atoms replaced by halogen, lower alkyl of 1 to 7 carbon atoms, for example, methyl, ethyl, propyl, butyl, pentyl, hexyl and the like, or lower alkoxy of 1 to 7 carbon atoms, for example, methoxy, ethoxy, propoxy, butoxy, or the like.

The o-nitrobenzylketones are prepared by reacting trans-$\beta$-substituted amino-2-nitrostyrene of the formula

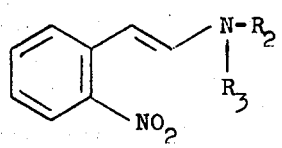   III wherein $R_2$ and $R_3$, independently, are lower alkyl or when taken together, are lower alkylene, with an acyl halide selected from the group consisting of lower alkanoyl halide, halo-lower alkanoyl halide, phthalimido-lower alkanoyl halide, benzoyl halide and substituted benzoyl halide to yield the corresponding compound of the formula

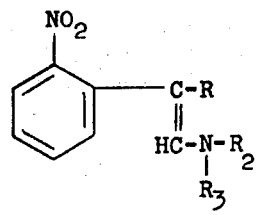   II wherein R is lower alkanoyl, halo-lower alkanoyl, phthalimido-lower alkanoyl, benzoyl or substituted benzoyl, and $R_2$ and $R_3$ are as previously described, and subsequently hydrolyzing the product of step (a) whereby the corresponding o-nitrobenzylketone of the forumula

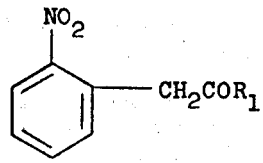   I wherein $R_1$ is lower alkyl, halo-lower alkyl, phenyl, substituted phenyl or phthalimido-lower alkyl,
is obtained.

The trans-$\beta$-substituted amino-2-nitrostyrenes of formula III are prepared by reacting o-nitrotoluene with a formamide acetal. The formamide acetals are known compounds or can be prepared by known procedures. Preferred formamide acetals are, for example, N,N-dimethylformamide diethyl acetal, N,N-dimethylformamide dimethyl acetal, N-formylpyrrolidine dimethyl acetal, 2-dimethylamino-1,3-dioxolane, N-formylpiperidine dimethyl acetal, N,N-dimethylformamide dibenzyl acetal, N,N-dimethylformamide dicyclohexyl acetal, N,N-dimethylformamide dineopentyl acetal, N,N-dimethylformamide di-isopropyl acetal, N,N-dimethylformamide di-n-heptyl acetal, and the like.

The condensation of the ortho-nitrotoluene with the formamide acetal can be effected in the presence or absence of an inert organic solvent. Preferably, the condensation is conducted in the presence of a polar aprotic solvent, such as, for example, N,N-dimethylformamide (DMF), diethyleneglycol dimethyl ether (Diglyme), hexamethylphosphortriamide (HMPT), and the like. The reaction conditions for the condensation are not narrowly critical. Thus, the condensation can be conducted at a temperature in the range of between about room temperature and the reflux temperature of the reaction mixture. Preferably, the reaction is conducted at a temperature in the range of 100°–160°. Most conveniently, the reaction is conducted at the reflux temperature of the reaction mixture. The condensation may be effected at atmospheric or superatmospheric pressures. Conveniently, it is effected at atmospheric pressure.

The acyl halides selected from the group consisting of lower alkanoyl halides, halo-lower alkanoyl halides, phthalimido-lower alkanoyl halides, benzoyl halides and substituted benzoyl halides are known compounds or can be prepared according to known procedures. Exemplary of such compounds are: acetyl chloride, propionyl chloride, bromoacetyl chloride, acid chloride of phthalimido glycine, benzoyl chloride, o-, m- or p-chlorobenzoyl bromide, o-, m- or p-methylbenzoyl chloride, 3,4-dichlorobenzoyl chloride, 3,4,5-trichlorobenzoyl chloride or the like.

A nitrostyrene of formula III is reacted, according to the invention, with a lower alkanoyl halide, halo-lower alkanoyl halide, phthalimido-lower alkanoyl halide, benzoyl halide or a substituted benzoyl halide to yield the corresponding compound of the formula

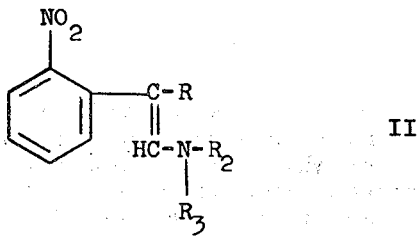

wherein R is lower alkanoyl, halo-lower alkanoyl, phthalimido-lower alkanoyl, benzoyl or substituted benzoyl, and wherein $R_2$ and $R_3$ are as previously described.

This reaction is carried out in an inert organic solvent, for example, an ether such as diethyl ether, dioxane, tetrahydrofuran or the like, aromatic hydrocarbons such as benzene, toluene, xylene or the like, or halogenated hydrocarbons such as methylene chloride, chloroform or the like, at a temperature in the range of from 0° to the reflux temperature of the reaction mixture. The compound of formula II can be isolated by known procedures prior to being hydrolyzed or can be hydrolyzed without isolation to yield the corresponding o-nitrobenzylketone of the formula

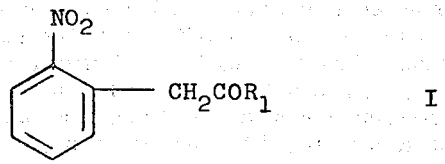

wherein $R_1$ is lower alkyl, halo-lower alkyl, phenyl, substituted phenyl or phthalimido-lower alkyl.

The hydrolysis is conveniently carried out by known procedures, for example, by treatment with water or mixtures comprising water and a water miscible organic solvent such as dioxane, tetrahydrofuran, alkanols, for example, methanol, ethanol, or the like. The hydrolysis is conveniently carried out at room temperature to the reflux temperature of the reaction mixture; reflux temperature is preferred.

The ketones of formula I are known compounds and are useful as intermediates in the preparation of useful indoles. The conversion of the compounds of formula I to the indoles can be effected by chemical or catalytic reduction, for example, utilizing sodium hydrosulfite, iron in acetic acid or the like, as chemical reducing agents or utilizing hydrogen in the presence of a catalyst such as Raney nickel, palladium or the like. The indoles prepared by the process of the invention have the formula

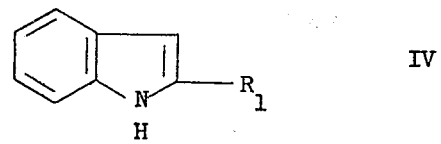

wherein $R_1$ is as previously described.

Exemplary of such known indoles are 2-methyl-indole, 2-phenyl-indole, 2-substituted phenyl-indole, and the like.

The following examples further illustrate the invention. All temperatures are in degrees Centigrade, unless otherwise mentioned.

EXAMPLE 1

Preparation of trans-β-dimethylamino-2-nitrostyrene

A solution of 34.3 g. of 2-nitrotoluene in a mixture of 37 g. of N,N-dimethylformamide diethylacetal and 100 ml. of dimethylformamide was heated under reflux for 26 hours. The dark reaction mixture was concentrated by first removing the lower boiling components on a rotary evaporator and then distilling the unreacted 2-nitrotoluene at about 75°/0.2 mm. The residual dark, red liquid (35 g., 72%), which was trans-β-dimethylamino-2-nitrostyrene, was used directly in the experiments below without further purification.

EXAMPLE 2

Preparation of 2'-fluoro-2-(2-nitrophenyl) acetophenone

To a stirred solution of 26.2 g. of trans-β-dimethylamino-2-nitrostyrene and 13.7 g. of triethylamine in 150 ml. of benzene there was added dropwise 21.8 g. of 2-fluorobenzoyl chloride. The resultant mixture was stirred and heated under reflux for 15 hours. Sufficient water was then added to dissolve the salts which had precipitated and the organic layer was separated and concentrated. The oil obtained was dissolved in a mixture comprising ml. of dioxane and 50 ml. of water and the resultant solution was heated under reflux for 18 hours and then concentrated. The residue was extracted with dichloromethane, dried and evaporated to an oil. The oil was dissolved in a small volume of cold ethanol and scratched to initiate crystallization. After refrigeration, filtration gave 18.5 g. of crude product. Filtration over 200 g. of florisil with benzene as the eluant yielded 16 g. (45%) of 2'-fluoro-2-(2-nitrophenyl)acetophenone as white crystals, m.p. 84°–86°. Recrystallization from carbon tetrachloride gave white prisms, m.p. 85°–86°.

Anal. Calcd. for $C_{14}H_{10}FNO_3$: C, 64.86; H, 3.89; N, 5.40. Found: C, 65.02; H, 4.03; N, 5.48.

EXAMPLE 3

Preparation of α-bromoacetyl-β-dimethylamino-2-nitrostyrene

To a stirred, ice-cooled solution of 38.4 g. of trans-β-dimethylamino-2-nitrostyrene and 16 g. of pyridine in 200 ml. of ether there was added dropwise 40.4 g. of bromoacetyl bromide dissolved in 50 ml. of ether. After stirring in an ice-bath for 1.5 hours, the suspension was filtered and the solid residue was washed with ether. The somewhat oily solid was partitioned between dichloromethane-water and the organic layer was separated, washed, dried and evaporated to dryness. The solid was recrystallized from dichloromethane-hexane to give amber needles, m.p. 125°–127°. The yield of α-bromoacetyl-β-dimethylamino-2-nitrostyrene was 44.6 g. (71%).

Anal. Calcd. for $C_{12}H_{13}BrN_2O_3$: C, 46.02; H, 4.18; N, 8.95. Found: C, 45.84; H, 4.48; N, 8.92.

EXAMPLE 4

Preparation of α-phthalimidoacetyl-β-dimethylamino-2-nitrostyrene

To a stirred suspension of 18.5 g. of potassium phthalimide in 700 ml. of warm dimethylformamide there was added 31.4 g. of α-bromoacetyl-β-dimethylamino-2-nitrostyrene. The resultant solution was stirred at room temperature for 2 hours and then was poured into 1 l. of ice-water. The precipitated solid was filtered, washed with water and recrystallized from methanol-dichloromethane to give 30 g. (79%) of α-phthalimidoacetyl-β-dimethylamino-2-nitrostyrene as orange prisms, m.p. 230°–233°. The microanalytical sample was obtained by an additional recrystallization from methanol-dichloromethane, m.p. 237°–239°.

Anal. Calcd. for $C_{20}H_{17}N_3O_5$: C, 63.32; H, 4.52; N, 11.08 Found: C, 63.34; H, 4.36; N, 11.24

EXAMPLE 5

Preparation of 1-(2-nitrophenyl)-3-phthalimido-2-propanone

A solution of 22.8 g. of α-phthalimidoacetyl-β-dimethylamino-2-nitrostyrene in a mixture of 950 ml. of dioxane and 50 ml. of water was heated under reflux for 70 hours and then evaporated at reduced pressure. The residue was extracted with dichloromethane, washed, dried and filtered over florisil. Elution with dichloromethane gave 10.6 g. (54%) of 1-(2-nitrohenyl)-3-phthalimido-2-propanone as a tan solid, m.p. 179°–182°. Recrystallization from methanol-dichloromethane yielded white needles, m.p. 181°–183°.

Anal Calcd. for $C_{17}H_{12}N_2O_5$: C, 62.96; H, 3.73; N, 8.64. Found: C, 63.02; H. 3.76; N, 8.71.

EXAMPLE 6

Preparation of 2-(2-fluorophenyl)indole

To 15.6 g. of 2'-fluoro-2-(2-nitrophenyl)acetophenone dissolved in a mixture of 150 ml. tetrahydrofuran, 150 ml. ethanol and 100 ml. water there was added portionwise 24 g. of sodium hydrosulfite. The mixture was stirred and heated on the steam bath for 10 minutes. Thereafter an additional 100 ml. of water was added and stirring was continued at room temperature for 20 minutes. At this point more sodium hydrosulfite (16 g.) was added portionwise. After warming, the mixture was stirred at room temperature for 20 minutes and evaporated at reduced pressure to remove the organic solvents. The solid which separated was filtered and washed with water. This aqueous filtrate was treated with 100 ml. of 6N hydrochloric acid and heated on the steam bath for 15 minutes. The resultant suspension was filtered and the two solids were combined and recrystallized from hexane (small amount undissolved was discarded) to give 5.9 g. (46%) of 2-(2-fluorophenyl)indole as white needles, m.p. 97°–98°.

Anal Calcd. for $C_{14}H_{10}FN$: C, 79.60; H, 4.77; N, 6.63. Found: C, 79.89; H, 4.72; N, 6.61.

EXAMPLE 7

Preparation of N-(2-indolylmethyl)phthalimide

A. Using the same procedure employed for the synthesis of 2-(2-fluorophenyl)indole 10 g. of 1-(2-nitrophenyl)-3-phthalimido-2-propanone was reduced with 20 g. of sodium hydrosulfite in a mixture of 300 ml. of ethanol, 250 ml. of tetrahydrofuran and 250 ml. of water. After removing the organic solvents, the aqueous solution was filtered and the resultant solid was suspended in 250 ml. of 8N sulfuric acid and 300 ml. of chloroform and warmed on the steam bath for 5 minutes. The organic layer was separated, washed, dried and concentrated to give 3.3 g. of N-(2-indolylmethyl)phthalimide as an off-white solid. Treatment of the original aqueous filtrate with sulfuric acid-chloroform in the same fashion gave an additional 0.9 g. of product. The total yield of N-(2-indolylmethyl)phthalimide was 4.2 g. (50%), m.p. 215°–219°. Recrystallization from acetonitrile gave pale-yellow needles, m.p. 226°–228.5°.

Anal Calcd. for $C_{17}H_{12}N_2O_2$: C, 73.90; H, 4.38; N, 10.14. Found: C, 74.01; H, 4.25; N, 10.14.

B. A solution of 20.7 g. of 1-(2-nitrophenyl)-3-phthalimido-2-propanone in 200 ml. of dimethylformamide was treated with about 10 g. of Raney nickel catalyst and the mixture was reduced in a Parr apparatus at an initial pressure of 46 psi. After hydrogen absorbtion ceased, the mixture was filtered and the dimethylformamide filtrate was evaporated to dryness. The residual solid was recrystallized from acetonitrile-dichloromethane to yield 11.4 g. (65%) of N-(2-indolylmethyl)phthalimide, m.p. 215°–220°, identical in all respects to the product obtained by method A).

EXAMPLE 8

Preparation of α-acetyl-β-dimethylamino-2-nitrostyrene

To a stirred solution of 3.84 g. of β-dimethylamino-2-nitrostyrene and 1.61 ml. of pyridine in 20 ml. of ether, was added dropwise a solution of 1.42 ml. of acetyl chloride in 5 ml. of ether. The mixture was stirred for 3 hours at 0° and filtered. The gummy solid was partitioned between methylene chloride and water. The organic phase was washed with dilute hydrochloride, dried and concentrated to a dark oil. The nmr spectrum was in agreement with the proposed structure. This product, i.e., α-acetyl-β-dimethylamino-2-nitrostyrene was used without further purification in the next step.

EXAMPLE 9

Preparation of 1-o-nitrophenyl-2-propanone

The product of Example 8, i.e., α-acetyl-β-dimethylamino-2-nitrostyrene was refluxed with a mixture of 8 ml. of water and 25 ml. of dioxane for 24 hours. After cooling, the mixture was concentrated in vacuo and the residue partitioned between methylene chloride and water. The organic phase was washed with brine, dried and concentrated. The crude product was chromatographed on silica gel using benzene, followed by methylene chloride as the eluent to give 926 mg. (26 percent based on β-dimethylamino-2-nitrostyrene) of 1-o-nitrophenyl-2-propanone as an oil. A small amount was recrystallized from hexane to give pale yellow plates of 1-o-nitrophenyl-2-propanone, having a melting point of 24°–25°. The nmr spectrum was in agreement with the proposed structure.

EXAMPLE 10

Preparation of 2-methylindole

To 500 mg. of 1-o-nitrophenyl-2-propanone dissolved in a mixture of 15 ml. of tetrahydrofuran, 15 ml. of ethanol and 10 ml. of water, was added portionwise 3 g. of $Na_2S_2O_4$ (sodium hydrosulfite). The mixture was stirred and heated on the steam bath for 10 minutes, then 10 ml. of water was added and the mixture stirred at room temperature for 20 minutes. Following the addition of 2 g. of $Na_2S_2O_4$ (sodium hydrosulfite), the solution was refluxed for 10 minutes and allowed to cool to room temperature. The solid which separated on cooling was filtered and recrystallized from ethanol/water to give 200 mg. (54 percent) of 2-methylindole as colorless plates, m.p. 57°–58°.

We claim:

1. A process for preparing o-nitrobenzylketone of the formula

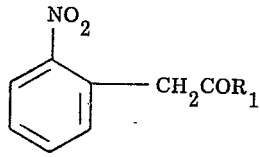

wherein $R_1$ is lower alkyl, halo-lower alkyl, phenyl, halogen-substituted phenyl, lower alkyl-substituted phenyl, lower alkoxy-substituted phenyl or phthalimido-lower alkyl,
which comprises the steps of:

a. reacting a trans-β-substituted amino-2-nitrostyrene of the formula

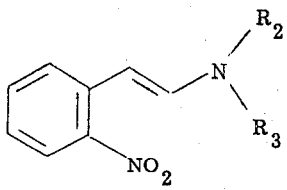

wherein $R_2$ and $R_3$, independently, are lower alkyl, or when taken together are lower alkylene,
with an acyl halide selected from the group consisting of lower alkanoyl halide, halo-lower alkanoyl halide, phthalimido-lower alkanoyl halide, benzoyl halide, halogen-substituted benzoyl halide, lower alkyl-substituted benzoyl halide and lower alkoxy-substituted benzoyl halide, to yield the corresponding compound of the formula

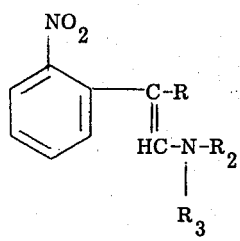

wherein R is lower alkanoyl, halo-lower alkanoyl, phthalimido-lower alkanoyl, benzoyl, halogen-substituted benzoyl, lower alkyl-substituted benzoyl or lower alkoxy-substituted benzoyl, and $R_2$ and $R_3$, independently, are lower alkyl, or when taken together, are lower alkylene,
at a temperature in the range of from 0° to the reflux temperature of the reaction mixture and subsequently, b. hydrolyzing the product of step (a) to yield a compound of the formula

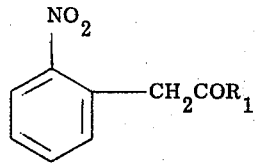

wherein $R_1$ is lower alkyl, halo-lower alkyl, phenyl, halogen-substituted phenyl, lower alkyl-substituted phenyl, lower alkoxy-substituted phenyl or phthalimido-lower alkyl.

2. A process in accordance with claim 1, wherein $R_2$ and $R_3$ are methyl.

3. A process in accordance with claim 1, wherein step (a) is carried out in an inert organic solvent.

* * * * *